US006242398B1

(12) United States Patent
Chambers et al.

(10) Patent No.: US 6,242,398 B1

(45) **Date of Patent: *Jun. 5, 2001**

(54) PROCESS FOR PRODUCING SOAP BARS

(75) Inventors: John George Chambers; Geoffrey Irlam; Bryan Stuart Joy, all of Bebington (GB)

(73) Assignee: Lever Brothers Company, division of Conopco, Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/137,007

(22) Filed: Aug. 20, 1998

(30) Foreign Application Priority Data

Aug. 28, 1997 (GB) ............................................ 9718235

(51) Int. Cl.[7] ............................................ A61K 7/50

(52) U.S. Cl. ......................... 510/151; 510/152; 510/155

(58) Field of Search .................................. 510/447, 130, 510/151, 152, 155

(56) References Cited

U.S. PATENT DOCUMENTS

| | | | | |
|---|---|---|---|---|
| 4,124,521 | | 11/1978 | Jedzinak . | |
| 4,941,990 | | 7/1990 | McLaughlin . | |
| 5,770,556 | | 6/1998 | Farrell et al. . | |
| 5,783,536 | * | 7/1998 | Farrell et al. | 510/141 |
| 5,801,139 | * | 9/1998 | Fair et al. | 510/447 |
| 5,817,609 | * | 10/1998 | He et al. | 510/133 |

FOREIGN PATENT DOCUMENTS

| | | |
|---|---|---|
| 0203750 | 12/1986 | (EP) . |
| 2001098 | 1/1979 | (GB) . |
| 96/312400 | 12/1988 | (JP) . |
| 92/08444 | 5/1992 | (WO) . |
| 95/02035 | 1/1995 | (WO) . |
| 96/29388 | 9/1996 | (WO) . |
| 97/40131 | 10/1997 | (WO) . |
| 97/47722 | 12/1997 | (WO) . |

OTHER PUBLICATIONS

International Search Report No. PCT/EP 98/05001, mailed Nov. 25, 1998.

* cited by examiner

*Primary Examiner*—Necholus Ogden
(74) *Attorney, Agent, or Firm*—Ronald A. Koatz

(57) ABSTRACT

A soap bar comprises 40–85% soap, 1–40% water immiscible benefit agent 1–40% solid water soluble carrier and 5–25% water. The carrier is initially mixed with the benefits agent to form a premix which is subsequently dispersed into the soap. Suitable benefit agents are oils and humectants whereas suitable carriers are starches, modified starches and water soluble solid polymers.

13 Claims, No Drawings

PROCESS FOR PRODUCING SOAP BARS

The invention relates generally to soap bars, and in particular to a process for producing soap bars comprising a benefit agent.

Toilet soap is the major product used for personal washing world-wide. Although the fat charge used to make such products varies enormously, the in-use properties vary little, apart from the amount of lather.

The bar sensory properties, i.e. lather quality and after-wash wet-skin feel, are totally unaffected by the fat charge. One of the main aims in recent years has been to find routes to modify bar sensory properties, especially the interaction of the product with skin. This aim is linked directly to consumer requirements for novel experiences from a bar product.

Early attempts in this direction relied upon addition of fatty acids to soaps which led to a modified lather creaminess, but provided no affect on the after-wash wet-skin feel. More recently some success has been had by addition of synthetic actives which because of their lime-soap dispersant action tend to modify the interaction of precipitated calcium and magnesium soaps with skin, and thereby modify the wet-skin feel of the product. This approach, although successful, does impose significant changes on fat charge in order to maintain acceptable bar processing and properties in the presence of high solubility synthetic actives.

A break-though in sensory delivery from toilet soaps would be one or more additives which could be incorporated into existing toilet soaps formulations using existing equipment, without the need for any modification in fat charge. This would enable such products to be processed at similar through-puts to conventional toilet soaps and, because of the use of identical fat charge, no disruption in wet soap manufacture in factories. Changing fat charge is a major issue in continuous soap manufacture, due to the fact that process control is extremely fat charge sensitive.

One approach which has been intensely studied by a number of workers is to incorporate an oil into the soap base. This has led to claims of a modicum of success but does have several drawbacks, i.e.— i. the soap mass becomes sticky and difficult to process due to oil coating soap and equipment; typical problems include poor feed into mills, low extrusion rates and die block.

ii. the finished product has a sticky feel and requires additional packaging to avoid contamination/leakage of oil into pack.

iii. the size of oil droplets in the product is extremely process sensitive, hence manufacture must be carefully controlled, i.e. reduced throughput is often necessary.

In general, this type of product can deliver sensory benefits but because of the aforementioned problems, it has not been commercially feasible.

It is an object of the invention to provide an improved process for making soap bars which overcomes at least some of the above problems.

We have discovered that incorporation of specific benefit agents into water soluble carriers can substantially correct or improve on all of the aforementioned process problems, and can lead to the production of bars at similar throughputs to conventional toilet soaps which have finishes comparable to conventional toilet soaps. In addition these products deliver modified lather and wet-skin feel sensory properties without any detrimental effects on general bar in-use properties such as amount of lather, wear-rate and mush.

The basis of this invention is that the benefit agent is first pre-blended into a solid carrier matrix so that its domain size is fixed, and constant throughout the process regime. This ensures that process effects on oil-droplet size are minimised, and hence ensures consistent delivery of sensory properties independent of process variation. Additionally, for benefit agents which can be solubilised by soap, (e.g. vegetable oils) the carrier effectively removes oil-migration through the product, and hence removes the risk of oil-solubilisation, since the oil is prevented from mixing with liquid material in the bar.

The carrier is selected from materials which are water soluble, and so dissolve to release the benefit agent during the washing process. We have also found that the delivery of sensory effects on wet-skin feel are significantly enhanced if the carrier dissolves via a viscous solution state, i.e. the carrier dissolves producing an initial substantial increase in viscosity (e.g. initial stages of polymer hydration). This viscous state during which benefit agent is released is key to delivery of a sensory effect to modify after-wash wet-skin feel. Typically carriers which meet this criteria have viscosities of a 60% carrier/water solution in excess of 1000 cps measured at a shear rate of $10s^{-1}$ at 20 degrees Celsius.

The soap of the current invention is typically comprised of non-lauric oils and lauric oils, ideally in a blend ratio of 95/5 to 10/90. Typical non-lauric oils include tallow, palm, tallow stearines, palm stearines, partially hardened vegetable oils and mixtures of these with partially or fully hardened oils. Typical lauric oils include coconut, palm kernel, and babassu oils. The soap base is generally produced by saponification of the oil blend using an appropriate alkali such as sodium, potassium, calcium and magnesium alkalis or combinations thereof. The soap base so made is ideally dried to a moisture content in the range 5–25% prior to addition of carrier-benefit-agent premix, or alternatively the carrier-benefit agent premix can be added to the neat soap prior to drying.

The carrier ideally exists as a solid at ambient and process conditions, hence its melting point preferably exceeds 80° C. The carrier is ideally wholly water soluble, and will ideally dissolve in water via a viscous liquid, where the viscosity of a 60% carrier/water solution is in excess of 1000 cps at a shear rate of $10s^{-1}$ at 20 Celsius. The viscous liquid state can be achieved by for example formation of liquid crystals or by molecular entanglement of long molecules, (e.g. polymers).

Examples of carriers which meet these requirements are maltodextrins, starches, modified starches, PVP's, PVA's, and cellulosic polymers, however other carriers which meet the above mentioned physical requirements are envisaged.

Preferred properties of the benefit agents are as follows. Firstly they should preferably be liquids at typical ambient wash temperatures and process temperatures, i.e. they should have a freezing point less than 30° C. Secondly, they should be essentially free of water to avoid dissolution of the carrier in the bar product, prior to washing with the product. Thirdly they should have a low viscosity, i.e. less than 60,000 cps, more preferably less than 30,000 cps. Fourthly they should ideally be immiscible with water.

Examples of benefit agents which meet these requirements are low viscosity silicone oils, vegetable oils, mineral oils, synthetic oils, (e.g. IPM, IPP), and mixtures thereof.

The benefit agent can be an "emollient oil", by which is meant a substance which softens the skin (stratum corneum) by increasing its water content, and keeping it soft by retarding decrease of water content.

Preferred emollients include:

(a) silicone oils, gums and modifications thereof such as linear and cyclic polydimethylsiloxanes; amino, alkyl alkylaryl and aryl silicone oils;

(b) fats and oils including natural fats and oils such as jojoba, soybean, rice bran, avocado, almond, olive, sesame, persic, castor, coconut, mink oils; cacao fat; lard; partially hardened oils obtained by hydrogenating the aforementioned oils; and synthetic mono, di and triglycerides such as myristic acid glyceride and 2-ethylhexanoic acid glyceride;

(c) waxes such as carnauba, spermaceti, lanolin and derivatives thereof;

(d) hydrophobic plant extracts;

(e) hydrocarbons such as liquid paraffins, Vaseline (trade mark), microcrystalline wax, ceresin, squalene, pristan and mineral oil;

(f) higher fatty acids such as oleic, linoleic, linolenic, lanolic, isostearic and poly unsaturated fatty acids (PUFA);

(g) higher alcohols such as lauryl, oleyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as ceramides, sucrose esters and pseudoceramides as described in European Patent Specification No. 556,957;

(k) sunscreens such as octyl methoxyl cinnamate (Parsol MCX) and butyl methoxy benzoylmethane (Parsol 1789);

(1) phospholipids; and (m) mixtures of any of the foregoing components.

A particularly preferred benefit agent is silicone, preferably silicones having viscosity less than about 60,000 centipoise. The silicone may be a gum and/or it may be a mixture of silicones. One example is polydimethylsiloxane having viscosity of about 60,000 centistokes.

The ratio of carrier to benefit agent is broadly between 1:4 and 4:1, preferably greater than or equal to 0.3:1, and more preferably greater than or equal to 0.75:1.

The invention will be more clearly understood from the following description of some examples thereof, given by way of example only.

Examples 1–5 below illustrate the invention where the carrier is a polyvinyl pyrrolidone, with a molecular weight of $8.0 \times 10^3$, and the benefit agent is selected from low viscosity silicone oils and sunflower oil. The ratio of carrier/benefit agent varies between 0.5:1 to 2:1. The manufacturing process is comprised of a pre-blending stage, where the carrier and benefit agent are mixed together in a suitable soft-solid mixer, (e.g. ribbon mixer or Z-blade mixer) followed by mixing of this blend into dried soap, again using either a ribbon or z-blade mixer, followed by conventional toilet soap finishing procedures, (i.e. milling, plodding and stamping into bars).

| | EXAMPLES | | | | |
|---|---|---|---|---|---|
| COMPONENT | 1 | 2 | 3 | 4 | 5 |
| Tallow/CNO = 80/20 comprised of sodium soap | 77.0 | 74.5 | 74.5 | 74.5 | 74.5 |
| Polyvinyl pyrrolidone | 2.5 | 5 | 5 | 5 | 5 |
| Silicone oil (5000 cps) | 5 | 5 | — | — | — |
| Silicone oil (12500 cps) | — | — | 5 | — | 2.5 |
| Sunflower oil | — | — | — | 5 | — |
| Perfume | 1.5 | 1.5 | 1.5 | 1.5 | 1.5 |
| Water and minors to 100% | | | | | |

All of the formulations of examples 1–5 have acceptable in-use properties comparable to conventional toilet soap. Moreover, sensory studies of formulations in Examples 1 and 4 showed both of these to have modified lather and wet-skin feel properties compared to conventional toilet soap.

The formulations of examples 6–10 below are included to further illustrate the lack of process effects of the carrier/benefit agent combinations. In these examples, the total additive level ranges from 10–20% by weight on product, and covers three carrier materials types, i.e. Maltodextrin and two tapioca starch derivatives. The bars were in all cases processed according to the method described for Examples 1–6, and the billet hardnesses were found to be virtually independent of carrier/benefit agent level, and very similar to the hardness of conventional toilet soap.

| | EXAMPLES | | | | |
|---|---|---|---|---|---|
| COMPONENT | 6 | 7 | 8 | 9 | 10 |
| Tallow/CNO soap | 74.5 | 69.5 | 64.5 | 69.5 | 69.5 |
| Maltodextrin (Grade) | 5 | 10 | 15 | — | — |
| Natrosorb-B* | — | — | — | 5 | — |
| Natrosorb-W* | — | — | — | — | 5 |
| Silicone oil (500 cps) | 5 | 5 | 5 | 10 | 10 |
| Perfume | 1.5 | 1.5 | 1.5 | 1.5 | 1.5 |
| Water and minors to 100% | | | | | |

*These materials are tapioca starch derivatives, available from National Starch.

Examples 11 to 14 below further illustrate the soap bar formulations according to the invention.

| | EXAMPLES | | | |
|---|---|---|---|---|
| COMPONENT | 11 | 12 | 13 | 14 |
| 80/20 tallow CNO soap | 74.5 | 74.5 | 74.5 | 74.5 |
| Maltodextrin | — | — | 5 | 5 |
| PVP | 5 | 5 | — | — |
| Isopropyl palmitate | 5 | — | 5 | — |
| Mineral oil | — | 5 | — | 5 |
| Perfume | 1.5 | 1.5 | 1.5 | 1.5 |
| Water and minors to 100% | | | | |

In Examples 15–19 formulations were given of carrier-benefit-agent systems which fall outside the scope of this invention. In all cases, the manufacturing method is identical to that used in the previous formulations of examples 1–10.

In Example 15 a water soluble benefit agent, glycerol, is incorporated at 1/1 ratio of carrier/benefit agent. Bars were produced of acceptable quality and hardness. In-use properties were found to be inferior to conventional toilet soap, with the formulation of the example having reduced lather amount. Sensory studies did not find any significant differences in lather quality or wet-skin feel from conventional toilet soaps.

In example 16, a carrier which dissolves directly into a low viscosity aqueous solution was used along with a modified soya bean oil. Bar production was found to be extremely difficult, due to billet cracking and poor bar cohesion. Bars produced were harder than conventional toilet soap and had poor surface finish. In-use properties of these products were found to be inferior to conventional toilet soap, having high wear-rates and low lather amount. Sensory studies did not find any significant differences in lather quality or wet-skin feel from conventional toilet soap.

In examples 17 and 18 a benefit agent which is comprised of a substantial amount of water, (ca 50%) was incorporated into a maltodextrin carrier. Manufacture was found to be extremely difficult, with the carrier-benefit agent pre-mix forming a viscous liquid which could not easily be mixed with the soap. Billets formed were softer and stickier than conventional toilet soap, and could not be stamped without use of a die-lubricant. Overall the formulation was clearly not suitable for processing on a continuous basis.

| | EXAMPLES | | | |
|---|---|---|---|---|
| COMPONENT | 15 | 16 | 17 | 18 |
| 80/20 tallow CNO soap | 74.5 | 54.5 | 74.5 | 64.5 |
| Maltodextrin | 5 | — | 5 | 10 |
| PEG8000 | — | 20 | — | — |
| Glycerol | 5 | — | — | — |
| Maleated soya-bean oil | — | 10 | — | — |
| Sodium Lactate solution | — | — | 5 | 10 |
| Perfume | 1.5 | 1.5 | 1.5 | 1.5 |
| Water and minors to 100% | | | | |

The invention is not limited to the examples and embodiments hereinbefore described which may be varied in both process step and detail without departing from the spirit of the invention, whilst remaining within the scope of the claims.

What is claimed is:

1. A process for producing a soap bar of the type comprising soap and a skin benefit agent, the process comprising the steps of:

(a) premixing a water immiscible benefit agent with a solid water soluble carrier, in a first mixing step; wherein the benefit agent is essentially free of water to avoid dissolution of the carrier and the carrier exists as a solid at ambient and process conditions so that the benefit agent is pre-blended into a matrix formed by the carrier such that a domain size of the benefit agent remains fixed and constant throughout the process;

(b) adding said pre-blended premix to a soap mix to form a final soap mix in a second mixing step; and (c) finalizing the final soap mix to form a soap bar.

2. A process as claimed in claim 1 in which during a washing step the carrier dissolves to release the skin benefit agent.

3. A process as claimed in claim 1 in which a 60% solution of carrier in water has a viscosity in excess of 1000 cps when measured at a shear rate of $10s^{-1}$ at 20° C.

4. A process as claimed in claim 1 in which the carrier is selected from the group comprising starches, modified starches and water soluble solid polymers.

5. A process as claimed in claim 1 in which the benefit agent is selected from oils and humectants.

6. A process as claimed in claim 5 in which the oil benefit agent is selected from silicone oils, natural triglyceride oils, mineral oils, synthetic oils, either in modified or non-modified forms.

7. A process as claimed in claim 1 in which the ratio of carrier to benefit agent is between 1:4 and 4:1.

8. A process as claimed in claim 1 in which during the second mixing step, the premix is added to neat soap prior to drying.

9. A process as claimed in claim 1 in which during the second mixing step, the premix is added to dried soap chips or the like.

10. A soap bar formed by a process according to claim 1.

11. A soap bar according to claim 10 comprising 40–85% soap, 1–40% carrier, 1–40% benefit agent, and 5–25% water.

12. A soap bar as claimed in claim 10 in which the soap is partially or wholly replaced by one or more of synthetic anionic surfactants, amphoteric surfactants or non-ionic surfactants or mixtures thereof.

13. A soap bar as claimed in any of claim 10 further including minor ingredients such as perfume and colorants.

* * * * *